United States Patent [19]

Shudo et al.

[11] 4,193,788
[45] Mar. 18, 1980

[54] N-(2-CHLORO-4-PYRIDYL)UREAS

[76] Inventors: Koichi Shudo, 2000-10-2-116 Kosugayacho, Totsukaku, Yokohama; Toshihiko Okamoto, 1-7-21 Shinoharakita, Kohokuku, Yokohama; Yo Isogai, 1-1-2-609, Kamiyoga, Setagayaku, Tokyo; Soshiro Takahashi, 904-10, Oaza, Kamiokubo, Urawashi, Saitama, all of Japan

[21] Appl. No.: 947,468

[22] Filed: Oct. 2, 1978

[30] Foreign Application Priority Data

Oct. 8, 1977 [JP] Japan .................. 52-121285

[51] Int. Cl.$^2$ .............. A01N 9/22; C07D 401/12; C07D 213/46; C07D 213/52
[52] U.S. Cl. ............................. 71/94; 71/74; 71/76; 71/92; 546/265; 546/305; 546/306
[58] Field of Search .............. 71/94, 76, 74; 546/306, 546/305, 265

[56] References Cited

U.S. PATENT DOCUMENTS

| | | | |
|---|---|---|---|
| 3,330,641 | 7/1967 | Woods et al. | 71/94 |
| 3,335,142 | 8/1967 | Hardy et al. | 546/265 |
| 3,426,031 | 2/1969 | Fischback | 546/306 |
| 3,682,934 | 8/1972 | Martin et al. | 71/94 |
| 3,687,959 | 8/1972 | Zielinski | 71/94 |
| 3,705,170 | 12/1972 | Torba | 71/94 |
| 3,992,391 | 11/1976 | Uno et al. | 546/305 |
| 4,149,872 | 4/1979 | Pilgram | 546/292 |

OTHER PUBLICATIONS

Deutsche Gold et al., "Substituted Pyridylureas." (1965), CA 65, pp. 15340-15341 (1966).

Primary Examiner—Glennon H. Hollrah
Attorney, Agent, or Firm—Gordon W. Hueschen

[57] ABSTRACT

N-(2-Chloro-4-pyridyl)ureas represented by the formula (I):

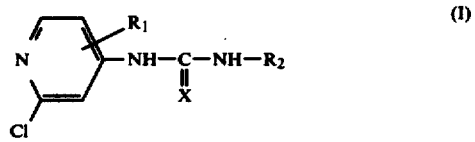

wherein $R_1$ represents hydrogen or alkyl, $R_2$ represents an aromatic group, especially phenyl, which may be substituted by alkyl, alkoxyl, hydroxyl or halogen, and X is oxygen or sulfur, and acid addition salts thereof, useful as plant growth regulators, are disclosed. Method of making and using same and agricultural compositions thereof are also disclosed.

20 Claims, No Drawings

N-(2-CHLORO-4-PYRIDYL)UREAS

BACKGROUND OF THE INVENTION

1. Field of the Invention

The invention relates to novel N-(2-chloro-4-pyridyl)ureas and thioureas represented by the formula(I) indicated hereinafter, agricultural compositions thereof, and a method of treating plants with them.

2. Brief Description of the Prior Art

British Pat. No. 1,122,662 discloses that some derivatives of urea can be used for preservation of plant materials. Further Proc. Roy. Soc., vol. B165, page 245, London(1966) reports that some ureas produce a desirable effect for developing the plantbud, while others show a mild effect as initiators of cell division.

SUMMARY OF THE INVENTION

This invention relates to novel N-(2-chloro-4-pyridyl)ureas and thioureas of formula(I) and acid addition salts thereof; a process for their preparation; a method of using the compounds and compositions for agricultural purposes, especially as plant growth regulators, and a process for the preparation of such compositions.

The novel compounds of formula(I) have valuable agricultural properties, especially growth-regulating effects as further elucidated hereinafter, which makes them useful as plant growth regulators.

DETAILED DESCRIPTION OF THE INVENTION

This invention relates to novel N-(2-chloro-4-pyridyl)ureas and thioureas, a process for their preparation, agricultural compositions which are useful as plant growth regulators containing one of the said compounds as an effective component thereof, and a method of treating plants therewith. Regulation of plant growth means acceleration or suppression of plant growth with a very small quantity of a chemical to regulate and control the state of plant growth as desired. Consequently, it does not indicate merely an increase or decrease in the height of a plant, but also the ability to have flowers or fruits when desired, or to obtain fruits without seeds, or to make the seeds dormant or conversely take them out of dormancy.

Control of plant growth with plant hormones is becoming an important technique in the agricultural and horticultural fields. Among the best and best-known plant growth regulators are cytokinine 6-(N-benzyl)adenine and kinetine.

One object of this invention is to provide plant growth regulators which have advantages over such known useful substances. Other advantages will become apparent hereinafter.

It has now been found that 4-pyridylureas and thioureas, which contain a chlorine atom in the 2-position of the pyridine ring, possess an extremely potent activity of the said type and have the ability to regulate plant growth over a wide range.

The active compounds provided by this invention comprise N-(2-chloro-4-pyridyl)ureas and thioureas having the following formula(I):

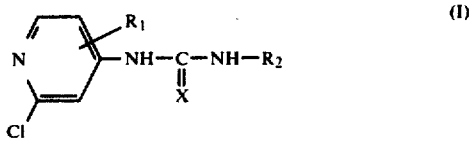

wherein $R_1$ represents hydrogen or alkyl of 1 to 3 carbon atoms, inclusive, such as methyl, ethyl, propyl and isopropyl; $R_2$ represents an aromatic group, preferably phenyl, pyridyl, naphthyl or biphenyl, which may be substituted by alkyl of 1 to 3 carbon atoms, inclusive, alkoxy of 1 to 3 carbon atoms, inclusive, hydroxyl, or halogen, especially one or two bromine, chlorine, or fluorine atoms; and X is oxygen or sulfur; and acid addition salts thereof.

Of these substituents, hydrogen and methyl for $R_1$, unsubstituted or methyl-substituted phenyl for $R_2$ and oxygen for X are preferred. The most preferred are hydrogen for $R_1$, unsubstituted phenyl for $R_2$ and oxygen for X. In the case of the halogen-substituted phenyl for $R_2$, the halogen is preferably chlorine and fluorine, more preferably chlorine.

The compounds represented by formula(I), wherein X represents oxygen, can be prepared by conventional methods. For brevity, reference is specifically made to the compound represented by formula(I), wherein $R_1$ is a hydrogen atom and $R_2$ is unsubstituted phenyl. Following conventional preparations, either (a) 2-chloro-4-aminopyridine is reacted with phenyl isocyanate, or (b) 2-chloro-4-pyridyl isocyanate is reacted with aniline, or (c) 2-chloro-isonicotinoylacide is reacted with aniline.

In carrying out this reaction, it is preferred to use a slight excess of one of the reactants, although approximately equivalent amounts of reactants may also be used in the usual suitable solvents. Some solvents for the reaction are benzene, toluene, xylene, acetone, methyl ethyl ketone, dimethylformamide, dimethylacetamide, dimethyl sulfoxide, chloroform, dichloromethane, tetrachloromethane, pyridine, and triethyl amine. An excess of aniline, when a reactant, is particularly useful as solvent. The reaction is favorably conducted in the range of −5° to 150° C., including room temperature, although it is most preferred to effect the reaction at the reflux temperature of the reaction mixture. A reaction time between five-tenths and five hours is sufficient to produce a good yield of desired product.

The compounds represented by the formula(I), wherein X represents sulfur can be also prepared by conventional methods illustrated in (a) and (b) by using the corresponding starting materials and under similar reaction conditions. However, as the reactivity and speed of the reaction for preparing thioureas is not as great when compared with the urea compounds, the reaction temperature should generally be in the range of 20° to 150° C.

The above-mentioned preparations (a), (b) and (c) can be represented by the following chemical reaction schemes:

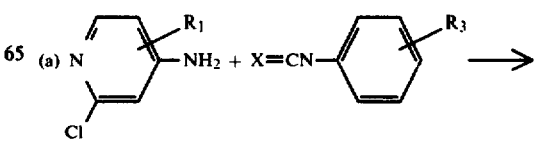

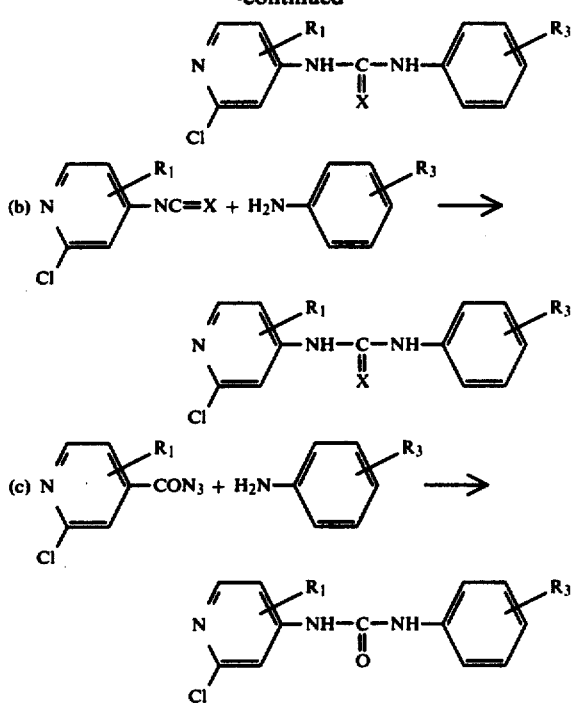

wherein $R_1$ and X have the same meanings as in formula(I) and $R_3$ represents lower alkyl, lower alkoxyl, hydroxyl, or halogen, especially bromine, chlorine or fluorine.

Some of the compounds of this invention are listed in the following:

N-(2-Chloro-4-pyridyl)-N'-phenylurea, N-(2-chloro-4-pyridyl)-N'-(2-chlorophenyl)urea, N-(2-chloro-4-pyridyl)-N'-(3-chlorophenyl)urea, N-(2-chloro-4-pyridyl)-N'-(4-chlorophenyl)urea, N-(2-chloro-4-pyridyl)-N'-(2-methylphenyl)urea, N-(2-chloro-4-pyridyl)-N'-(3-methylphenyl)urea, N-(2-chloro-4-pyridyl)-N'-(4-methylphenyl)urea, N-(2-chloro-4-pyridyl)-N'-(2,5-dichlorophenyl)urea, N-(2-chloro-4-pyridyl)-N'-(2-fluorophenyl)urea, N-(2-chloro-4-pyridyl)-N'-(4-n-propylphenyl)urea, N-(2-chloro-4-pyridyl)-N'-(2-ethoxyphenyl)urea, N-(2-chloro-4-pyridyl)-N'-phenylthiourea, N-(3-bromo-4-pyridyl)-N'-phenylurea, etc.

The N-(2-chloro-4-pyridyl)ureas and thioureas of this invention possess accelerating action on cell mitosis, cell enlargement, and cell differentiation, and are effective in the acceleration of fruiting, prevention of fruit and flower from falling, growth acceleration, and growth suppression. By adjusting the concentration of the chemical employed, a marked suppression of growth(herbicidal) can be caused to occur at a high concentration of the chemical.

The action, field of application, use, and plants to which these chemicals are applicable, are listed in the following table (Table A). The most prominent effective use of these chemicals is found in the increased nuber of fruits in pepos such as melon and watermelon, inhibition of flower shedding, accelerated growth of green vegetables, extension of tobacco leaf area, and herbicidal effect(when desired).

Table A

| Action | Application, Use | Plants to be applied |
|---|---|---|
| 1. Acceleration of fruit bearing | Increased fruits (flowers) (fruit) | pepos, tomato, eggplant, apple, Japanese pear, citrus, apricot, soybean |
| Prevention of fruit falling | Inhibition of flower shedding | grape |
| 2. Acceleration of fruit falling and defoliation | Picking fruits (picking excess fruits to increase fruit yield and to make fruit size uniform) | citrus, plum, peach, apple, tomato, pineapple |
|  | Picking flowers (excess flowers picked to increase fruit yield and to make fruit size uniform) | apricot, Japanese pear, plum, peach |
|  | Defoliation (to remove leaves for easier harvesting of cotton and soybeans) | cotton, soybean |
| 3. Growth acceleration | Acceleration of root growth and taking root | cuttage |
|  | Growth acceleration(stalk, leaves, roots) | vegetables |
|  | Increased size of fruit(increase in commercial value by larger size of fruit) | citrus, apple, apricot |
|  | Increased tillering, accelerated bud formation | soybean, pineapple |

Table A-continued

| Action | Application. Use | Plants to be applied |
| --- | --- | --- |
| | Accelerated flowering | flowering plants |
| 4. Growth suppression | Suppression of height | trees, grass, flowering plants |
| | Suppression of lodging | paddy rice, wheat |
| | Suppression of budding | potato, onion |
| | Suppression of tillering (prevention of excess growth) | soybean |
| 5. Organ Formation | Renewal of new branches(buds) | rose, fruit tree seedlings |
| 6. Others | Herbicidal effect | |
| | Desiccation | cotton |
| | Increased sugar content | sugar cane, sugar beet |

The urea derivatives of this invention show the same activity in concentrations only a fraction of that required with 6-(N-benzyl)adenine and kinetin, which have hitherto been considered the most potent plant growth regulating substances available. Even in comparison with N-(4-pyridyl)-N'-phenylurea of similar structure, they show a 100-fold or greater increase in activity. This increased activity is unexpectedly observed only when a chlorine atom is present at the 2-position of the pyridine ring.

To explain in more concrete terms, in the test for tobacco callus growth, the optimal concentration to give miximum yield of callus is 0.01 ppm for 6-(N-benzyl)adenine and 0.1 ppm for N-(4-pyridyl)-N'-phenylurea, whereas that of the potent N-(2-chloro-4-pyridyl)ureas of this invention is only 0.0005 to 0.001 ppm. Generally, substitution on the phenyl ring decreases the activity in the tobacco test for the acceleration of cell differentiation, the optimal concentration of 6-benzyladenine being 10 ppm, but less than 1 ppm of N-(2-chloro-4-pyridyl)ureas gives formation of numerous shoots.

N-(2-Chloro-4-pyridyl)ureas of this invention show the effect of increasing weight, not only in callus cells but also on pith tissue, leaf tissue, and on plants during growth.

The plant growth regulators of this invention can be applied to plants and crops in general, but are especially effective when applied to a member of the *leguminosae, solanaceae, unbelliferae, popes vitaceal, cucurbitaceae* and *vitaceae* families.

The amount of a compound of this invention to be used by spraying the plant directly is generally 100 to 1000 liters per Ha as a solution of a concentration of 0.0001 to 10,000 ppm, preferably 0.01 to 10,000 ppm. When used in soil, an amount 5- to 100-fold of that give above is required. It goes without saying that the amount to be applied will differ according to the object of the control and the plant to which applied. For example, 100 to 1000 liters of a solution of the following concentration should be used per Ha.

| | |
| --- | --- |
| For growth acceleration and increased fruiting | 0.01–1,000 ppm |
| For growth acceleration of callus | 0.0001–100 ppm |
| For acceleration of fruit falling and defoliation | 0.1–10,000 ppm |
| For growth suppression and herbicidal | 10–more than 10,000 ppm |

The compounds of this invention can be used alone or in admixture with other substances or compositions having effective components, such as other plant regulators, herbicides, insecticides, fungicides, and acericides, usually in the form of solutions, emulsions, wettable powders, granules, fine granules, or powders.

The preparation of suitable compositions may be carried out in known manner, as by mixing, for example, 0.1 to 50%, preferably 0.1 to 10%, of a compound of this invention with a bulking agent, such as a liquid or solid diluent or carrier and, if necessary, using an emulsifying agent or dispersing agent. As substances preferably as a liquid diluent or a carrier may be cited water, aromatic hydrocarbons such as xylene, benzene, and methylnaphthalene, chlorinated aromatic hydrocarbons such as chlorobenzene, mineral oil fractions such as paraffin, alcohols such as methanol and propanol, and polar solvents such as dimethylformamide and acetone. Among the substances preferably as a solid diluent or carrier are, for example, talc, clay, kaolin, white carbon, wood powder and sand. As an emulsifying agent may be used polyoxyethylene-fatty acid esters or polyoxyethylene-fatty acid alcohol ethers. Dispersing agents include alkyl sulfonates, alkyl aryl sulfonates, alkali metal salts, alkaline earth metalsalts, ammonium salt of lignin-sulfonic acid, and methylcellulose.

These compounds or preparations thereof per se may be added to a medium or applied directly to the plant or onto the surface of leaves or stalks thereof, or sprayed on the soil, but are usually applied in the form of the usual preparations thereof. Further, the plant growth controlling agents of this invention may be added together with fertilizers and/or extenders.

These compounds can also be used in the form of an inorganic or organic salt such as the hydrochloride, phosphate, or sulfate thereof.

The following examples and preparations are given by way of illustration only, and are not to be construed as limiting.

Some representative examples of preparative forms will be given below.

| | |
| --- | --- |
| Preparation 1. | Wettable powder |
| | N-(2-Chloro-4-pyridyl)-N'- |

| Preparation | Ingredient | % |
|---|---|---|
| | phenylurea | 1% |
| | Sodium β-naphthalenesulfonate-formaldehyde condensate | 2% |
| | Polyoxyethylene alkyl aryl ether | 2% |
| | Clay | 95% |

These ingredients are ground, mixed and diluted with water.

| Preparation 2. | Emulsion | |
|---|---|---|
| | N-(2-Chloro-4-pyridyl)-N'-(3-chlorophenyl)urea | 1% |
| | Xylene | 74% |
| | Polyoxyethylene alkyl aryl ether | 4.5% |
| | Alkyl aryl sulfonate | 0.5% |
| | Isophorone | 20% |

The above ingredients are mixed to dissolve and the resulting solution is emulsified in water.

| Preparation 3. | Liquid | |
|---|---|---|
| | N-(2-Chloro-4-pyridyl)-N'-(2-chlorophenyl)urea | 1% |
| | Dimethylformamide | 94% |
| | Polyoxyethylenesorbitan monolaurate | 5% |
| | | Parts by Weight |
| Preparation 4. | Granule | |
| | N-(2-Chloro-4-pyridyl)-N'-(3-methylphenyl)urea | 5 |
| | Bentonite | 15 |
| | Talc | 47.5 |
| | Clay | 30 |
| | Sodium dodecylbenzene sulfonate | 0.5 |
| | Sodium ligninsulfonate | 2 |
| Preparation 5. | Emulsion | |
| | N-(2-Chloro-4-pyridyl)-N'-(3-methylphenyl)urea | 5% |
| | Xylene | 70% |
| | Polyoxyethylene alkyl aryl ether | 4.5% |
| | Alkyl aryl sulfonate | 0.5% |
| | Isophorone | 20% |

These ingredients are mixed, ground, mixed with 25 parts of water, and made into granules using an extrusion-granulation apparatus. The granules are then dried and sieved. These granules are sprayed per se.

| Preparation 6. | Wettable powder | |
|---|---|---|
| | N-(2-Chloro-4-pyridyl)-N'-(3-methylphenyl)urea | 5% |
| | Sodium -naphthalenesulfonate-formaldehyde condensate | 3% |
| | Polyoxyethylene alkyl aryl ether | 3% |
| | Clay | 89% |
| Preparation 7. | Solution | |
| | N-(2-Chloro-4-pyridyl)-N'-(3-chlorophenyl)urea | 100 ppm |
| | Acetone | 20% |
| | Water | 80% |

SYNTHESIS 1

Manufacture of N-(2-chloro-4-pyridyl)-N'-phenylurea (1) To a solution of 257 mg. (2 mmol) of 2-chloro-4-aminopyridine dissolved in ten ml. of dry acetone, 238 mg. (2 mmol) of phenyl isocyanate is added and the mixture is stirred at room temperature for 8 hrs. The solvent is evaporated under a reduced pressure, the residue is chromatographed over alumina, and the column is developed with chloroform. Eluates containing the objective substance are collected, and the solvent is evaporated under a reduced pressure. The residue is recrystallized from acetone-ether mixture and 364 mg. of N-(2-chloro-4-pyridyl)-N'-phenylurea is obtained. Yield, 73.5%, mp 173°-174° C.

| Analysis for $C_{12}H_{10}ClN_3O$ | C | H | N |
|---|---|---|---|
| Calcd. | 58.19 | 4.07 | 19.69 |
| Found | 58.27 | 4.15 | 16.93 |

(2) To a solution of 365 mg. (2 mmol) of 2-chloroisonicotinoyl azide dissolved in 10 ml. of dry benzene, 186 mg. (2 mmol) of aniline is added and the mixture is refluxed for 3 hrs. When cooled, the solvent is evaporated under a reduced pressure and the residue is chromatographed over alumina. The column is developed with chloroform and eluates containing the objective substance are collected. The solvent is evaporated under a reduced pressure and the residue is recrystallized from acetone-ether mixture to 453 mg. of N-(2-chloro-4-pyridyl)-N'-phenylurea, mp 183°-184° C. Yield, 91.4%.

The following compounds were also prepared in the same manner.

| Compound | mp (°C.) |
|---|---|
| N-(2-Chloro-4-pyridyl)-N'-(2-chlorophenyl)urea | 183 |
| N-(2-Chloro-4-pyridyl)-N'-(3-chlorophenyl)urea | 198-199 |
| N-(2-chloro-4-pyridyl)-N'-(4-chlorophenyl)urea | 201-201.5 |
| N-(2-Chloro-4-pyridyl)-N'-(2-methylphenyl)urea | 184-185 |
| N-(2-Chloro-4-pyridyl)-N'-(3-methylphenyl)urea | 93-95 |
| N-(2-Chloro-4-pyridyl)-N'-(4-methylphenyl)urea | 188.5-190 |
| N-(2-Chloro-4-pyridyl)-N'-(2,5-dichlorophenyl)urea | 215-216 |
| N-(2-Chloro-4-pyridyl)-N'-(2-fluorophenyl)urea | 186-187 |
| N-(2-Chloro-4-pyridyl)-N'-(4-n-propylphenyl)urea | 156-157 |
| N-(2-Chloro-4-pyridyl)-N'-(2-ethoxyphenyl)urea | 96-99 |
| N-(2-Chloro-4-pyridyl)-N'-phenylthiourea | 141-142 |

EXAMPLE 1

Test on Growth Effect of N-(2-chloro-4-pyridyl)-N'-phenylurea on Tobacco Callus Cells Tobacco callus was cultured in Murashige-Skoog medium containing 0.0001 to 0.1 ppm of N-(2-chloro-4-pyridyl)-N'-phenylurea and 2 ppm of indoleacetic acid as auxin, for 30 days at a temperature of about 26° C. Final weight of fresh callus is shown in Table I. The control was a tabacco callus cultured in the Murashige-Skoog medium containing only auxin, under the same condition. For the sake of comparison, values obtained in a medium containing optimal amount 6-(N-benzyl)adenine are also given in Table I. Values are all an average of six individuals.

Table I

| | Concentration (ppm) | Weight (mg) |
|---|---|---|
| N-(2-Chloro-4-pyridyl)-N'-urea | 0.0001 | 782 |
| " | 0.001 | 4,991 |
| " | 0.01 | 1,235 |
| " | 0.1 | 519 |
| Benzyladenine | 0.01 | 5,150 |
| Control | | 153 |

EXAMPLE 2

Test on Growth Effect of N-(2-Chloro-4-pyridyl)-N'-(3-methylphenyl)urea on Tobacco Callus Tobacco callus was cultured in the same way as in Example 1 and the results shown in the following Table II were obtained.

Table II

|  | Concentration(ppm) | Weight(g.) |
| --- | --- | --- |
| N-(2-Chloro-4-pyridyl)-N'-(3-methylphenyl)urea | 0.001 | 1,784 |
| N-(2-Chloro-4-pyridyl)-N'-(3-methylphenyl)urea | 0.01 | 6,760 |
| N-(2-Chloro-4-pyridyl)-N'-(3-methylphenyl)urea | 0.1 | 4,945 |
| N-(2-Chloro-4-pyridyl)-N'-(3-methylphenyl)urea | 1 | 1,508 |
| Control |  | 153 |

The use of N-(2-chloro-4-pyridyl)-N'-(3-chlorophenyl)urea gave a similar result.

EXAMPLE 3

Test on Shoot Formation Effect on N-(2-Chloro-4-pyridyl)-N'-phenylurea from Pith Tissue:

Section(s) of tobacco pith tissue were inoculated in Murashige-Skoog medium containing 0.01 to 10 ppm of N-(2-chloro-4-pyridy)-N'-phenylurea. This was cultured at a temperature of about 26° C. for 30 days, and the number of pith sections forming shoots was counted. For comparison, benzyladenine was tested in a similar way. Results are shown in Table III.

Table III.

| Conc. (ppm) | Shoot Formation from Pith Sections Shoot Formation* | |
| --- | --- | --- |
|  | 6-(N-Benzyl)-adenine | N-(2-Chloro-4-pyridyl)-N'-phenylurea |
| 10 | 1/24 | 10/24 |
| 1 | 12/24 | 13/24 |
| 0.1 | 2/24 | 10/24 |
| 0.01 | 0/24 | 0/24 |

*Number of pith sections with shoots/number of pith sections planted. One to six shoots are formed from one pith section.

EXAMPLE 4

Test on Shoot Formation from Callus Cells by N-(2-Chloro-4-pyridyl)-N'-(2-methylphenyl)urea Tobacco callus was inoculated in Murashige-Skoog medium containing 0.01 to 10 ppm of N-(2-chloro-4-pyridyl)-N'-phenylurea. This was cultured at room temperature for 30 days, and the number of callus with shoot formation was counted. For comparison, benzyladenine was tested in a similar way. Results are shown in Table IV.

Table IV.

| Concn. (ppm) | Shoot Formation from Tobacco Callus Shoot Formation Rate* | |
| --- | --- | --- |
|  | Benzyladenine | N-(2-Chloro-4-pyridyl)-N'-(2-methylphenyl)urea |
| 10 | 12/12$^a$ | 10/12$^a$ |
| 1 | 12/12$^a$ | 9/12$^a$ |
| 0.1 | 2/12$^b$ | 1/12$^b$ |

Table IV.-continued

| Concn. (ppm) | Shoot Formation from Tobacco Callus Shoot Formation Rate* | |
| --- | --- | --- |
|  | Benzyladenine | N-(2-Chloro-4-pyridyl)-N'-(2-methylphenyl)urea |
| 0.01 | 0/12 | 0/12 |

*Number of callus forming shoots/number of callus inoculated
$^a$Number of shoots, 50-70(size of individual shoots, 1-3 cm.)
$^b$Number of shoots, 1-10(size of individual shoots, 0.5-1 cm)

EXAMPLE 5

Test on Shoot Formation from Callus by N-(2-Chloro-4-pyridyl)-N'-phenylurea

Medium solutions containing 0.0001 to 1 ppm of N-(2-chloro-4-pyridyl)-N'-phenylurea were prepared and tobacco callus culture was carried out as in Example 4. The results obtained are shown in Table V.

Table V.

| Concn. (ppm) | Shoot Formation from Tobacco Callus Shoot Formation Rate* | |
| --- | --- | --- |
|  | Benzyladenine | N-(2-Chloro-4-pyridyl)-N'-phenylurea |
| 10 | 12/12$^a$ | — |
| 1 | 12/12$^a$ | 12/12$^a$ |
| 0.1 | 2/12$^b$ | 12/12$^a$ |
| 0.01 | 0/12 | 12/12$^a$ |
| 0.001 | — | 2/12$^b$ |
| 0.0001 | — | 0/12 |

*Number of callus section forming shoots/number of callus sections inoculated
$^a$Number of shoots, 50-70(size of individual shoots, 1-3 cm.)
$^b$Number of shoots, 1-10(size of individual shoots, 0.5-1 cm.)

EXAMPLE 6

Test on Increase in Size of Leaves of Green Vegetable by N-(2-Chloro-4-pyridyl)-N'-phenylurea Solutions containing 10, 1, and 0.1 ppm of N-(2-chloro-4-pyridyl)-N'-phenylurea in water were prepared. To 50 ml. of each solution placed in a petrie dish, 10 pieces of the leaf of Brassica repa var. pervidis which were round leaves of a 10 mm. diameter and cut out with a corkborer, were floated on the surface of the solution, one group being in contact with the solution with the back of the leaf and the other group being in contact with the surface of the solution with the surface of the leaf. The dishes were allowed to stand at room temperature for 8 days, and diameter and weight of each leaf pieces determined. The control leaves were left in water. These results are shown in Table VI.

Table VI

| With Back of the Leaf in Contact with Water | | | With Surface of the Leaf in Contact with Water | | |
| --- | --- | --- | --- | --- | --- |
| Concn. (ppm) | Diameter (mm) | Weight (mg) | Concn. (ppm) | Diameter (mm) | Weight (mg) |
| 10 | 13.7 | 30.5 | 10 | 13.2 | 26.8 |
| 1 | 13.5 | 32.1 | 1 | 14.2 | 31.1 |
| 0.1 | 14.2 | 33.3 | 0.1 | 13.9 | 28.1 |
| Control | 12.1 | 21.7 | Control | 11.9 | 21.0 |

EXAMPLE 7

Test on Acceleration of Fruit Bearing in Pepos

Watermelon(variety 'Yamato') raised outdoors was used as test plant. Artificial pollination was made at the peak of flowering, and a solution of the selected chemical in desired concentration was pinted or sprayed on the gynophore. Fruit-bearing rate was examined two weeks after the treatment.

Table VII

| Treatment | Chemical | Concentration (ppm) | Fruit-bearing rate (%) |
|---|---|---|---|
| Painting | N-(2-Chloro-4-pyridyl)-N'-phenylurea | 1,000 | 100 |
|  | BA (liquid)* | 1,000 | 65 |
|  | " | 10,000 | 100 |
|  | None |  | 43 |
| Spraying | N-(2-Chloro-4-pyridyl)-N'-phenylurea | 1,000 | 90 |
|  | " | 500 | 87 |
|  | " | 100 | 82 |
|  | BA(liquid)* | 10,000 | 83 |
|  | None |  | 35 |

*BA(liquid) is a liquid containing 3% benzyladenine [i.e., 6-(N-benzyl)aminopurine]; same as hereafter

EXAMPLE 8

Test on Suppression of Height and Extension of Leaf Area in Tobacco Plant

Seedlings of tobacco(variety, Bright Yellow) were transplanted in unglazed pots of about 13 cm. in diameter and the pots were left in a greenhouse. Solutions of the selected chemical of desired concentration were sprayed with a sprayer, 15 ml. for each pot, homogeneously on leaves and stalk at the time when 6 to 8 leaves were out. One section of the pots was sprayed once and the other section three times at 13-day intervals. Examination of the result was made when middle leaves started to become yellow (35 days after the initial spraying of the chemical), and height of the plant, fresh weight of stalk and leaves, and average area of five lower leaves were measured, and ratio of these values to those of the non-treated plants was calculated. Experimental section was three pots per area and their average was taken. Results are listed in the following Table VIII.

Table VIII

| Compound tested | Concn. (ppm) | No. of sprayings | Percent to Non-treated Area | | |
|---|---|---|---|---|---|
|  |  |  | Height | Fresh Weight | Leaf Area |
| N-(2-Chloro-4-pyridyl)-N'-phenylurea | 500 | 1 | 74 | 171 | 158 |
|  |  | 3 | 42 | 169 | 145 |
| 5% WP* | 100 | 1 | 78 | 188 | 175 |
|  |  | 3 | 72 | 206 | 185 |
|  | 20 | 1 | 102 | 178 | 172 |
|  |  | 3 | 98 | 160 | 152 |
| BA(liquid) | 500 | 1 | 99 | 151 | 118 |
|  |  | 3 | 85 | 138 | 111 |
|  | 100 | 1 | 98 | 118 | 141 |
|  |  | 3 | 90 | 115 | 124 |
|  | 20 | 1 | 106 | 109 | 120 |
|  |  | 3 | 98 | 113 | 121 |
| None (%) |  |  | 100 | 100 | 100 |
| " |  |  | (74.6 cm) | (126.6 g/stock) | (278 cm²/leaf) |

*5% WP: Wettable power containing 5% N-(2-chloro-4-pyridyl)-N'-phenylurea

EXAMPLE 9

Inhibition of Flower Shedding and Acceleration of Fruit Bearing in Grape

Grapevine (variety Delaware) raised in plastic house covering was used for the examination. N-(2-Chloro-4-pyridyl)-N'-phenylurea or benzyladenine (200 or 100 ppm) was added to 100 ppm of gibberelline solution, and recemose flowers were dipped in each solution (April 14). Ten days after full bloom (May 4), all the fruit clusters were again soaked and treated with 100 ppm solution of gebberelline. The grapevines were then left to usual cultivation conditions until harvest. Grapes were harvested on June 29, and weight of each cluster, length of cluster, density of berries, number of berries on each cluster, and berry diameter were measured. These values were compared with those found with grapes with gebberelline treatment alone. Experimental area contained two new brances, three repetition, and average value of fifteen fruit clusters was calculated. Results are shown in Table IX Table IX Effect on Inhibition of Flower Shedding of Delaware-Grape (Average of 15 Clusters)

| Items Examined Compound added to GA (100 ppm) Soln. | concn. (ppm) | Weight of Berry Cluster (g) | Length of One Cluster (cm) | Density of Berries (No./cm) | No. of Berries per Cluster (No.) | Seedless Berries (%) | Diameter of Gynophore (mm) | Weight of Gynophore (g) | Hardness of Gynophore (feel) |
|---|---|---|---|---|---|---|---|---|---|
| N-(2-Chloro-4-pyridyl)-N'-phenylurea | 200 | 195.6 (190) | 13.7 (91) | 14.3 (210) | 136.6 (194) | 100 | 5.08 (213) | 5.96 (248) | Hard |
|  | 100 | 196.3 (190) | 14.5 (97) | 13.5 (199) | 136.3 (194) | 100 | 5.60 (192) | 5.47 (228) | slightly hard to hard |
|  | 50 | 189.8 (184) | 14.4 (94) | 13.5 (199) | 129.6 (184) | 100 | 4.62 (193) | 4.71 (196) | slightly hard to hard |
|  | 25 | 180.8 (175) | 15.0 (100) | 13.5 (178) | 129.6 (202) | 100 | 3.82 (160) | 4.71 (196) | slightly hard to hard |
| BA 3% Soln. | 200 | 136.8 (132) | 14.8 (99) | 9.2 (135) | 93.3 (133) | 100 | 3.82 (139) | 2.75 (115) | Ordinary |
|  | 100 | 125.3 (122) | 15.5 (103) | 8.1 (119) | 73.9 (105) | 100 | 3.02 (126) | 2.46 (103) | slightly soft to ordinary |
| GA alone | (100) | 103.1 (100) | 15.0 (100) | 6.8 (100) | 70.3 (100) | 100 | 2.39 (100) | 2.40 (100) | slightly soft |

BA = 6-(N-benzyl)aminopurine.
GA = Gibberellin
Values in parentheses denote percentage to the values obtained with the use of GA alone.

EXAMPLE 10

Test on Herbicidal Effect

Soil containing the subterranean stems of narrowleaf waterplantain (*Alisma canaliculatum*) and bulrush (*Scirpus juncoides*) homogeneously was filled in ceramic pots of 30 cm in diameter. Seeds of barnyard grass (*Echinochloa crus-balli*), umbrella plant (*Cyperus diformis*) were each sown in pots, fifty seeds to each pot. Then paddy rice seedlings (Variety Kinmaze) at the two-leaf stage was planted, five seedlings per pot, and the pots were filled with water so as to have a water layer of three cm. above the soil. When the barnyard grass reached the one-leaf stage, the desired quantity of the solution of the selected test chemical(s), prepared according to Preparation 1, was sprayed uniformly over the surface of the water. Herbicidal effect was examined fourteen days after the chemical treatment. Result of this test was expressed by the following index (Table X):

Table X

5: Complete control of weeds
4: Over 80% control of weeds
3: Over 60% control of weeds
2: Over 40% control of weeds
1: Over 20% control of weeds
0: No effect

| Compound | Amount (kg/Ha) | Control of Weeds | | | | Narrow leaf water plantain | Effect on paddy rice |
|---|---|---|---|---|---|---|---|
| | | Barnyard grass | Unbrella plant | Monochoria | Bulrush | | |
| N-(2-Chloro-4-pyridyl)-N'-phenylurea | 1 | 5 | 5 | 5 | 4 | 5 | 0 |
| | 0.5 | 4 | 4 | 4.5 | 3 | 4.5 | 0 |

EXAMPLE 11

Test on Increase of Leaf and New Brances in Datura Sunguinea

Datura Sunguinea sp. (average height of 8 cm.) were transplanted outdoors. Solutions of the chemically desired concentration were sprayed with a sprayer, 15 ml. each plant, on the leaves and stalk of the plant at the time when the average height of the plant was 20 cm. Three weeks later, the plants were harvested and the height of the plant and the total weight of fresh leaves and stalks on the new brances were measured. Average values of five plants are listed in Table XI.

Table XI

| Compound | Concn. (ppm) | Height (cm) | Total Weight (g) | New Branches (g) |
|---|---|---|---|---|
| N-(2-Chloro-4-pyridyl)-N'-phenyl-urea | 20 | 80 | 450 | 80 |
| N-(2-Chloro-4-pyridyl)-N'-phenyl urea | 100 | 75 | 500 | 100 |
| BA(liquid) | 500 | 90 | 402 | 70 |
| Control | | 103 | 348 | 40 |

EXAMPLE 12

Test on Increase of Leaf and New Branches in Datura Sunguina

Datura Sunguina sp. (average height of 8 cm.) were transplanted outdoors and test using N-(2-chloro-4-pyridyl)-N'-(3-bromophenyl)urea were conducted as in Example 11. The results shown in Table XII were obtained.

Table XII

| Compound | Concn. (ppm) | Height (cm) | Total Weight (g) | New Branches (g) |
|---|---|---|---|---|
| N-(2-chloro-4-pyridyl)-N'-(3-bromo-phenyl)urea | 60 | 81 | 450 | 78 |
| N-(2-chloro-4-pyridyl)-N'-(3-bromo-phenyl)urea | 300 | 74 | 490 | 98 |
| BA(liquid) | 500 | 91 | 391 | 68 |
| Control | | 102 | 352 | 41 |

Various modifications and equivalents will be apparent to one skilled in the art and may be made in the compounds, compositions and methods of the present invention without departing from the spirit or scope thereof, and it is therefore to be understood that the invention is not to be limited to the specific examples and embodiments disclosed herein.

What is claimed is:

1. A compound selected from the group consisting of N-(2-chloro-4-pyridyl)ureas of the following formula.

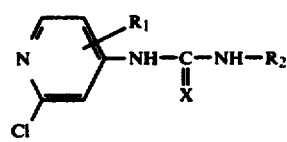

wherein $R_1$ represents hydrogen or alkyl of from 1 to 3 carbon atoms, inclusive; $R_2$ represents aryl selected from the group consisting of phenyl, pyridyl, naphthyl, and biphenyl, which may be substituted by alkyl of from 1 to 3 carbon atoms, inclusive; alkoxy; of from 1 to 3 carbon atoms, inclusive; hydroxyl or halogen; and X stands for oxygen or sulfur; and acid addition salts thereof.

2. An N-(2-chloro-4-pyridyl)urea as claimed in claim 1 wherein X is an oxygen atom.

3. An N-(2-chloro-4-pyridyl)urea as claimed in claim 1 wherein $R_1$ is hydrogen.

4. A compound of claim 1 which is selected from the group consisting of N-(2-chloro-4-pyridyl)-N'-phenylurea and an acid addition salt thereof.

5. An agricultural composition useful as a plant growth regulator comprising as active ingredient a compound selected from the group consisting of an N-(2-chloro-4-pyridyl)urea of claim 1, of the formula:

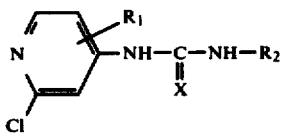

wherein $R_1$ represents hydrogen or alkyl of from 1 to 3 carbon atoms, inclusive; $R_2$ represents aryl selected from the group consisting of phenyl, pyridyl, naphthyl, and biphenyl, which may be substituted by alkyl of from 1 to 3 carbon atoms, inclusive; alkoxy of from 1 to 3 carbon atoms, inclusive; hydroxyl or halogen; and X is oxygen or sulfur; and an acid addition salt thereof, in an effective plant-growth regulating amount, together with an inert carrier or diluent.

6. The agricultural composition of claim 5 which further contains an emulsifying or dispersing agent.

7. The agricultural composition of claim 5 wherein said N-(2-chloro-4-pyridyl)urea is present in a herbicidally-effective amount.

8. A method of controlling plant growth which comprises contacting a plant or part thereof with a compound selected from the group consisting of an N-(2-chloro-4-pyridyl)urea of claim 1, of the formula:

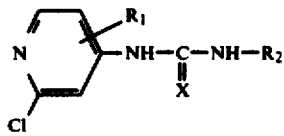

wherein $R_1$ represents hydrogen or alkyl of from 1 to 3 carbon atoms, inclusive; $R_2$ represents aryl selected from the group consisting of phenyl, pyridyl, naphthyl, and biphenyl, which may be substituted by alkyl of from 1 to 3 carbon atoms, inclusive; alkoxy of from 1 to 3 carbon atoms, inclusive; hydroxyl or halogen; and X is oxygen or sulfur; and acid addition salt thereof, in an amount effective for regulation of the growth of the plant involved.

9. The method of claim 8, wherein the compound is in admixture with an inert carrier or diluent.

10. The method of claim 8, wherein the compound is contacted with the plant in a herbicidally-effective amount thereof.

11. The composition according to claim 5, wherein X is oxygen and $R_2$ is phenyl.

12. The composition according to claim 11, wherein $R_1$ is hydrogen.

13. The method of controlling plant growth according to claim 8, wherein X is oxygen and $R_2$ is phenyl.

14. The method of controlling plant growth according to claim 13, wherein $R_1$ is hydrogen.

15. A compound of claim 1, wherein X is sulfur.

16. A compound of claim 1, wherein $R_2$ is pyridyl.

17. A composition of claim 5, wherein X is sulfur.

18. A composition of claim 5, wherein $R_2$ is pyridyl.

19. A method of claim 8, wherein X is sulfur.

20. A method claim 8, wherein $R_2$ is pyridyl.

* * * * *